(12) United States Patent
Jha et al.

(10) Patent No.: US 11,295,433 B2
(45) Date of Patent: Apr. 5, 2022

(54) IOT BASED APPARATUS FOR ASSESSING QUALITY OF FOOD PRODUCE

(71) Applicant: JIDDU, INC., Sunnyvale, CA (US)

(72) Inventors: Miku Jha, Sunnyvale, CA (US); Amitava Bhaduri, Sunnyvale, CA (US)

(*) Notice: Subject to any disclaimer, the term of this patent is extended or adjusted under 35 U.S.C. 154(b) by 58 days.

(21) Appl. No.: 16/612,587

(22) PCT Filed: Oct. 4, 2018

(86) PCT No.: PCT/US2018/054270
§ 371 (c)(1),
(2) Date: Nov. 11, 2019

(87) PCT Pub. No.: WO2019/177663
PCT Pub. Date: Sep. 19, 2019

(65) Prior Publication Data
US 2020/0410662 A1    Dec. 31, 2020

Related U.S. Application Data

(60) Provisional application No. 62/642,594, filed on Mar. 13, 2018.

(51) Int. Cl.
*G06K 9/00* (2022.01)
*G06T 7/00* (2017.01)
(Continued)

(52) U.S. Cl.
CPC ....... *G06T 7/0004* (2013.01); *G01N 21/8851* (2013.01); *G01N 33/025* (2013.01);
(Continued)

(58) Field of Classification Search
CPC ......... G06T 2207/30128; G06T 7/0004; G06T 2207/30024; G06T 7/0012;
(Continued)

(56) References Cited

U.S. PATENT DOCUMENTS

| 5,526,437 A | 6/1996 | West |
| 6,234,006 B1 | 5/2001 | Sunshine |

(Continued)

FOREIGN PATENT DOCUMENTS

| CN | 103325041 B | 9/2013 |
| CN | 207866803 U | 9/2018 |

(Continued)

OTHER PUBLICATIONS

Medus, "Hyperspectral image classification using CNN: Application to industrial food packaging," 2021, Elsevier (Year: 2021).*

(Continued)

*Primary Examiner* — Alex Kok S Liew (57) ABSTRACT

An IoT based apparatus to assess the quality of food or agricultural produce is disclosed. The apparatus comprises a frame having an enclosure, a movable tray disposed at a middle portion of the enclosure, one or more camera installed within the enclosure, one or more light source strategically mounted within the enclosure to avoid reflection and hot spots, at least one storage unit, a touch screen display and a single board computer coupled to the camera, light source, storage unit and touch screen display. The enclosure is illuminated by the light source and the camera is configured to capture the image of the produce from both the top and bottom side of the produce. A pre-trained deep learning model is used on both the top and bottom view images to identify defects in the agricultural produce. The identified defects are displayed to the user via the touch screen display.

20 Claims, 9 Drawing Sheets

(51) Int. Cl.
*H04N 5/232* (2006.01)
*G01N 21/88* (2006.01)
*G01N 33/02* (2006.01)
*G06T 5/50* (2006.01)
*H04N 5/225* (2006.01)
*H04N 5/247* (2006.01)
*G06V 20/20* (2022.01)
*G16Y 10/05* (2020.01)
*G16Y 10/45* (2020.01)
*G01N 21/84* (2006.01)
*G06V 20/68* (2022.01)

(52) U.S. Cl.
CPC ............... *G06T 5/50* (2013.01); *G06V 20/20* (2022.01); *H04N 5/2253* (2013.01); *H04N 5/2256* (2013.01); *H04N 5/23299* (2018.08); *H04N 5/247* (2013.01); *G01N 2021/8466* (2013.01); *G01N 2021/8887* (2013.01); *G01N 2201/062* (2013.01); *G01N 2201/0634* (2013.01); *G06T 2207/20221* (2013.01); *G06T 2207/30128* (2013.01); *G06V 20/68* (2022.01); *G16Y 10/05* (2020.01); *G16Y 10/45* (2020.01)

(58) Field of Classification Search
CPC . G06T 2207/10056; G06T 2207/10024; G06T 7/001; G06T 7/0006; G06T 7/90; G06T 2207/10016; G06T 2207/10064; G06T 2207/10116; G06T 7/12; G06T 7/62; G06T 2207/10028; G01N 33/12; G01N 21/94; G01N 33/02; G01N 23/04; G01N 21/31; G01N 2021/8887; G01N 21/274; G01N 21/6456; G01N 21/8851; G01N 2223/618; G01N 2291/02475; G01N 23/083; G06K 9/00; G06K 9/4652; G06K 2209/17; G06K 9/00127; G06K 9/00577; G06K 9/0014; G06K 9/00147

See application file for complete search history.

(56) References Cited

U.S. PATENT DOCUMENTS

| | | | |
|---|---|---|---|
| 6,450,008 | B1 | 9/2002 | Sunshine |
| 6,668,240 | B2 | 12/2003 | Singh |
| 7,014,816 | B2 | 3/2006 | Miller |
| 7,350,403 | B2 | 4/2008 | Yakhno |
| 9,087,333 | B2 | 7/2015 | Kim |
| 9,538,880 | B2 | 1/2017 | Riefenstein |
| 9,815,191 | B2 | 11/2017 | Oleynik |
| 10,200,834 | B2 | 2/2019 | Tran |
| 10,327,583 | B2 | 6/2019 | Hiatt |
| 2002/0118106 | A1 | 8/2002 | Brenn |
| 2005/0203353 | A1 | 9/2005 | Ma |
| 2006/0057022 | A1 | 3/2006 | Williams |
| 2008/0253648 | A1* | 10/2008 | Mulder ............... B07C 5/3422 382/165 |
| 2008/0284902 | A1 | 11/2008 | Konno |
| 2009/0080706 | A1* | 3/2009 | Tao ..................... G06T 7/0004 382/110 |
| 2009/0236334 | A1 | 9/2009 | Ben-Shmuel |
| 2010/0112680 | A1 | 5/2010 | Brockwell |
| 2011/0035326 | A1 | 2/2011 | Sholl |
| 2011/0236862 | A1 | 9/2011 | Culver |
| 2012/0016814 | A1 | 1/2012 | Evans |
| 2012/0321759 | A1 | 12/2012 | Marinkovich |
| 2014/0293091 | A1* | 10/2014 | Rhoads ................. G01J 3/513 348/234 |
| 2014/0366639 | A1 | 12/2014 | Naito et al. |
| 2016/0123948 | A1 | 5/2016 | Bar-Or |
| 2016/0203591 | A1 | 7/2016 | Justaniah |
| 2017/0074522 | A1 | 3/2017 | Cheng |
| 2019/0009940 | A1 | 1/2019 | Scarabelli |

FOREIGN PATENT DOCUMENTS

| | | |
|---|---|---|
| CN | 209102410 U | 7/2019 |
| IN | 201841002429 A | 2/2018 |
| IN | 201711011848 A | 6/2018 |
| JP | 2003106995 A | 4/2003 |
| KR | 20160000831 A | 1/2016 |

OTHER PUBLICATIONS

"IOT for Agriculture; Food Quality and Safety", https://iopscience.iop.org/article/10.1088/1757-899X/343/1/012023/pdf.

"A Next Generation Sensing and Monitoring Platform for Quality Assessment of Perishable Foods", https://beyondstandards.ieee.org/iot/a-next-generation-sensing-and-monitoring-platform-for-quality-assessment-of-perishable-foods/

"Arduino Based Smart IoT Food Quality Monitoring System", https://www.engineersgarage.com/contributions/arduino-based-smart-iot-food-quality-monitoring-system/.

"An Intelligent IoT-Based Food Quality Monitoring Approach Using Low-Cost Sensors", https://www.researchgate.net/publication/331738835 An Intelligent IoT-Based Food Quality Monitoring Approach Using Low-Cost Sensors.

"Application of Internet of Things to the Monitoring System for Food Quality Safety", https://ieeexplore.ieee.org/abstract/document/6597990.

"Top Applications for IoT in the Food and Beverage Retail Industry", https://dzone.com/articles/top-applications-for-Iot-in-the-food-amp-beverage.

"IOT based Smart Food Monitoring System", http://troindia.in/journal/ijcesr/vol6iss6/73-76.pdf.

"Perishable Food Quality Monitoring—An Internet of Things (IoT) Approach", https://acadpubl.eu/jsi/2017-115-6-7/articles/7/10.pdf.

"IoT Sensors Keep Fresh Food Safe", https://innovate.ieee.org/innovation-spotlight/iot-sensor-supply-chain-food/.

"ITreck: IoT framework for Smart Food Monitoring System", https://www.ijcaonline.org/archives/volume148/number12/srivastava-2016-ijca-911314.pdf.

"Novel Equipment for Food Quality Control: an IoT Nanowire Gas Sensors Array", https://www.aidic.it/cet/19/75/005.pdf.

"Chapter 10—Internet of things-linked wearable devices for managing food safety in the healthcare sector", https://www.sciencedirect.com/science/article/pii/B9780128153697000100.

"Food Industry Unplugged", https://www.foodqualityandsafety.com/article/food-industry-unplugged/?singlepage=1.

"The design of food quality supervision platform based on the Internet of Things", https://ieeexplore.ieee.org/abstract/document/6199193.

* cited by examiner

IOT BASED APPARATUS FOR ASSESSING QUALITY OF FOOD PRODUCE

CROSS REFERENCE TO RELATED APPLICATIONS

The present application claims the benefit of PCT Patent application PCT/US18/54270 filed on 4 Oct. 2018 entitled "IoT BASED APPARATUS FOR ASSESSING QUALITY OF FOOD PRODUCE" which further claims the benefit of U.S. Patent Application 62/642,594 "IoT Based Apparatus for Assessing Quality of Food Produce", filed Mar. 13, 2018, the contents of which is hereby incorporated by reference.

BACKGROUND OF THE INVENTION

A. Technical Field

The present invention generally relates to assessment of food quality. More specifically, the present invention relates to an IoT based apparatus for inspecting the quality of food produce.

B. Description of Related Art

Agricultural produce or food produce presents different market values according to their quality. Such quality is usually quantified in terms of freshness of the products, as well as the presence of contaminants (pieces of shell, husk, and small stones), surface defects, mould and decays. Quality attribute also relates to the appearance of the product and include properties such as such as color, shape and size. The consumer assesses these quality attributes and consciously or unconsciously assigns a score and then mentally calculates an overall quality score for future purchase decisions. They determine the purchase behavior of consumers, as these properties may be inspected readily by the eye. The assessment of quality attributes is thus an essential component.

Assessment of food quality of fresh produce is currently done by food quality inspectors by visual inspection and knowledge subject to human interpretations. As a result, the interpretations lack the objectivity, prone to introduce human biases and visual errors. Further, Manual assessment is labor intensive and time-consuming process. Patent reference US20150109451, to Mukul Dhankhar entitled "Automated object recognition kiosk for retail checkouts" relates to automating the object recognition process at kiosks using a system, method and an apparatus. The system includes a controller, memory and an imaging device, which communicates to the controller. The software communicates to the controller and receives the image of the object and extract at least one feature from the image to perform object detection based on a predetermined model using machine learning method. The system also uses an illumination device of a predetermined level of brightness to illuminate the object to take images and process the same. The system includes a display device to show the detected objects.

Patent reference US20080253648, to Steven C. Mulder et al, entitled "Food product checking system and method for identifying and grading food products" relates to a food product checking system for identification and grading of food products packed in a tray. The system comprising a tray positioning area, an illumination device for illuminating the food product with white light, at least one camera for taking images of the illuminated food product, and an evaluation device for image processing of taken images and to perform a color analysis of taken images.

Patent reference U.S. Pat. No. 8,031,910, to Michael A. Jones et al, entitled "Method and apparatus for analyzing quality traits of grain or seed" relates to an apparatus for measuring and selecting grain for use in milling, or seed for use in plant breeding. The apparatus utilizes an illumination device and camera and performs color image analysis of seed/grain sample(s) to characterize multiple quality traits. However, the foregoing patent reference offers restrictive solutions by capturing only the top view of the image and providing an uncontrolled and inconsistent open work surface.

Therefore, there is a need for an apparatus for food produce quality assessment and grading which uses images taken from both the top and bottom views by adjustable cameras inside a controlled enclosure. The consistency of the controlled environment need to be driven using LED strips with a color characteristic of warm white with a temperature of 3000K-3500K.

SUMMARY OF THE INVENTION

Embodiments in accordance with the present invention provide an IoT (Internet of Things) based apparatus for inspecting the quality of agricultural produce, agricultural product or food produce.

In an embodiment, the IoT based apparatus for inspecting quality of food produce, comprising a frame having an enclosure, a movable tray disposed at a middle portion of the enclosure, one or more camera installed within the enclosure, one or more light source strategically mounted within the enclosure to avoid reflection and hot spots, at least one storage unit, a touch screen display and a single board computer coupled to one or more camera, one or more light source, and the touch screen display.

The movable tray is configured to receive and place the agricultural product to be assessed. In an embodiment, one or more camera comprises a first camera installed at an upper portion of the enclosure and a second camera installed at a lower portion of the enclosure. In an embodiment, one or more light source comprises a first light source disposed at the top portion of the enclosure and a second light source disposed at the lower portion of the enclosure. In an embodiment, at least one storage unit is configured to store the image of food produce from one or more camera. In an embodiment, the touch screen display is configured to display the food produce placed in the tray. In an embodiment, the single board computer is configured to: light the first light source to emit light and capture image of an upper region of the food produce placed in the tray; light the second light source to emit light and capture image of a lower region of the food produce placed in the tray; store the at least two captured image in the storage unit and analyze the at least two captured images to obtain defect value of the food produce, using a deep learning model; and display the defect value and the food produce image along with defects labelled on the image.

In another embodiment, the IoT apparatus connected with an internet could be connected to other devices like tablets, smartphones and other embedded devices. This will help in distributing the defect analysis scores and the defects labeled on the images to every interested party in the food supply chain for a particular produce.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF EMBODIMENTS

A description of embodiments of the present invention will now be given with reference to the Figures. It is expected that the present invention may be embodied in other specific forms without departing from its spirit or essential characteristics. The described embodiments are to be considered in all respects only as illustrative and not restrictive.

Figure 1:
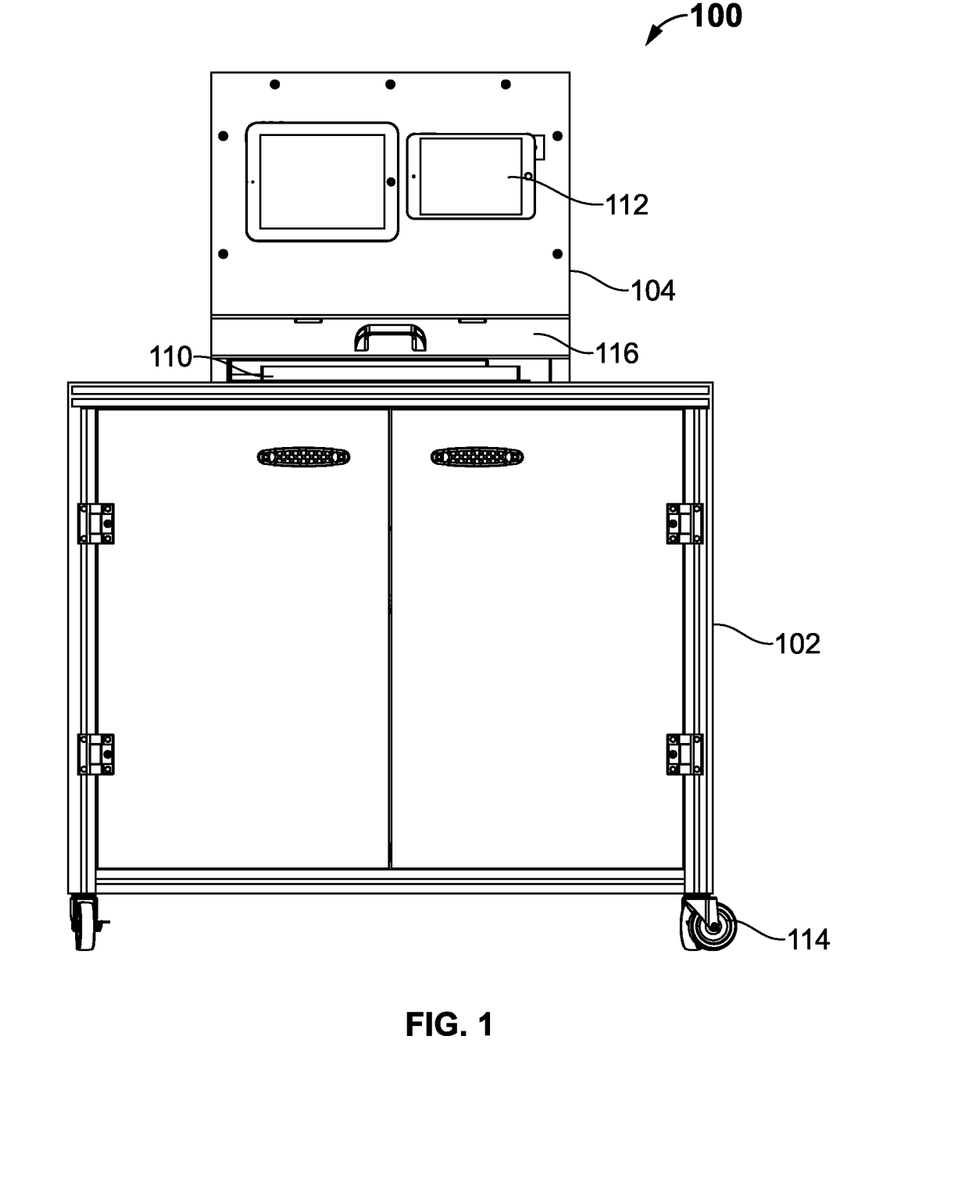
FIG. 1 exemplarily illustrates a front view of the IoT based apparatus for assessing the quality of the food produce, according to the present invention.

The present invention discloses an IoT based apparatus 100 for assessing the quality of food produce such as fruits or veggies, like strawberries, blueberries, raspberries, blackberries, bananas, peach, apricot, apple, tomatoes, spinach, lettuce etc., as shown in FIG. 1, incorporating the aspects of the present invention. The IoT based apparatus 100 uses deep learning algorithms to do defect identification like bruises, decay, discoloration, mold, mildew, shape anomalies on the monotonic image. The IoT apparatus 100 is further configured to provide defect analysis scores for the assessed food produce. In an example, the apparatus 100 identifies defects in an image of one or more strawberries, but the image is not contaminated by the presence of other food items. Referring to FIGS. 1 to 6, the IoT based apparatus 100 comprises different components; such as: one or more camera, camera mounts 117 for mounting one or more camera, one or more light source, a movable clear plastic tray 110, a frame 102, an enclosure 104, one or more wheels 114, a touch screen display 112 and a single board computer (SBC) 118 (shown in FIG. 7) coupled to one or more camera, one or more light source, and the touch screen display 112.

In an embodiment, the SBC 118 is configured to drive the one or more light source and one or more camera in sequence to capture at least two images of the food produce placed in the clear plastic tray 110, wherein the at least two image includes top and bottom side of the food produce. One or more light source is positioned to properly illuminate the food produce and to avoid undue light reflections from the tray 110. The tray 110 has a light transmission capability of ~92%, which is perfect to capture image from a bottom camera through the clear plastic tray 110. Further, the choice of using the light source with a color temperature of around 5500-degree kelvin, which is close to natural sunlight and color rendering index (CRI) of >90 to preserve the natural color of fruits and vegetables. In one embodiment, a color characteristic of the light source is chosen depending on the use case and to accentuate the bright colors of fruits and vegetables. In another embodiment, the light source emits a warm white color with a temperature of 3000K-3500K. The SBC 118 including programming/object detection algorithm to flip one of the images and performs offset correction to properly align with the first image. The object detection algorithm could exactly localize the top view and bottom view of the food produce for the deep learning model to perform the defect detection unambiguously. The technique of superimposing the top and bottom view leads to almost 360-degree coverage of the food produce, which helps in the assessment of food quality inspection.

Figure 2:
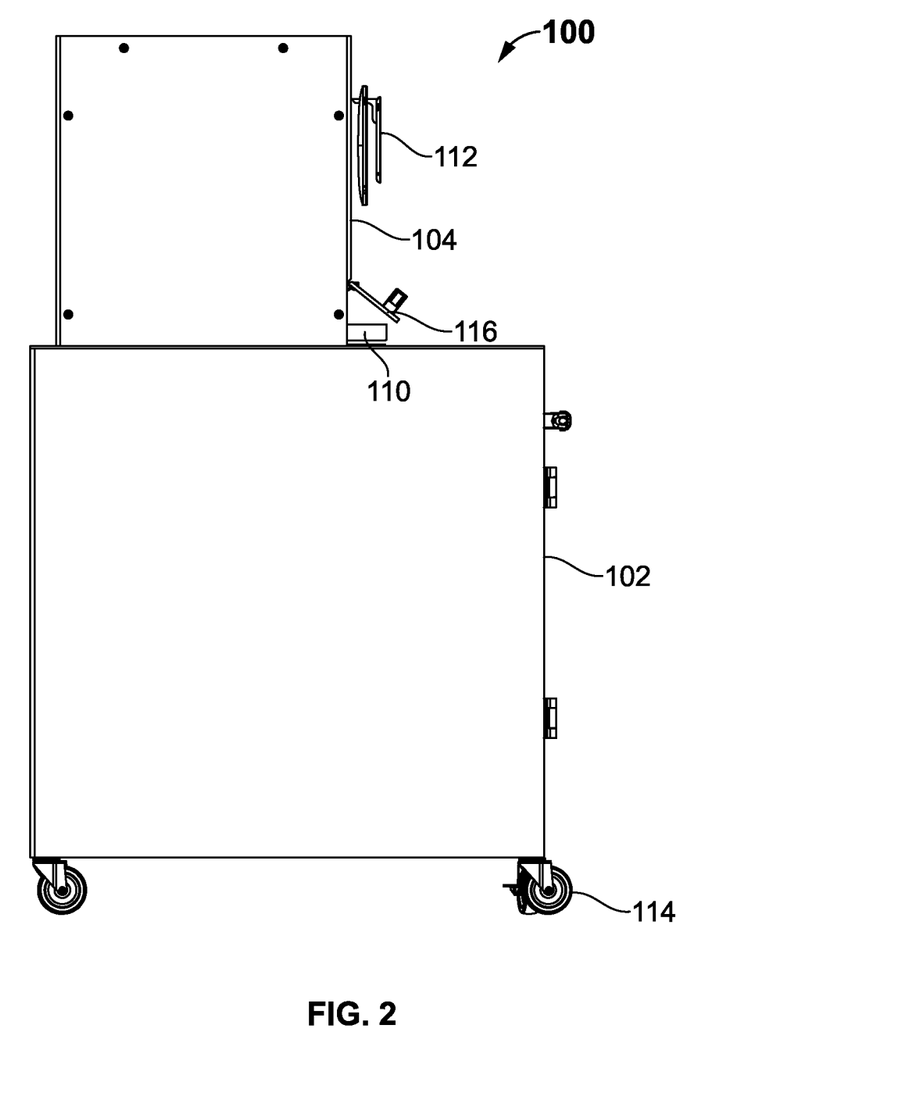
FIG. 2 exemplarily illustrates a side view of the IoT apparatus for assessing the quality of the food produce in an embodiment of the present invention.

FIG. 2 exemplarily illustrates a side view of the IoT based apparatus 100 for assessing the quality of the food produce, in an embodiment of the present invention. In an embodiment, the IoT based apparatus 100 further comprises one or more wheels 114 beneath the frame 102 to facilitate movement of the apparatus 100. One or more camera and one or more light source are mounted within the enclosure 104. The IoT based apparatus 100 is manufactured with the movable tray 110 to contain the food produce for inspection. The movable tray 110 is disposed at a middle portion of the enclosure 104.

Figure 3:
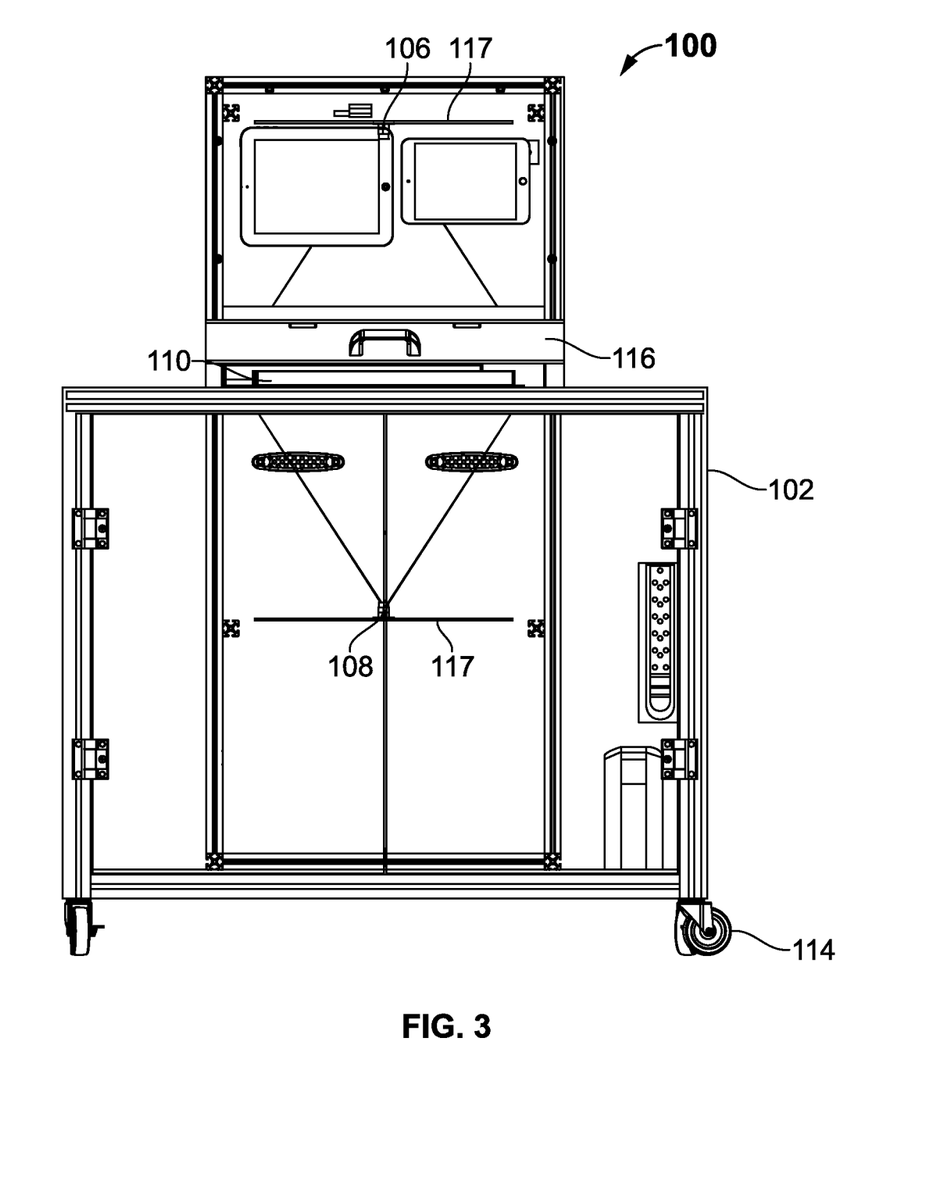
FIG. 3 exemplarily illustrates a see-through front view of the IoT apparatus for assessing the quality of the food produce in another embodiment of the present invention FIG. 4 exemplarily illustrates a side cross sectional view of the IoT apparatus for assessing the quality of the food produce, in an embodiment of the present invention.
Figure 4:
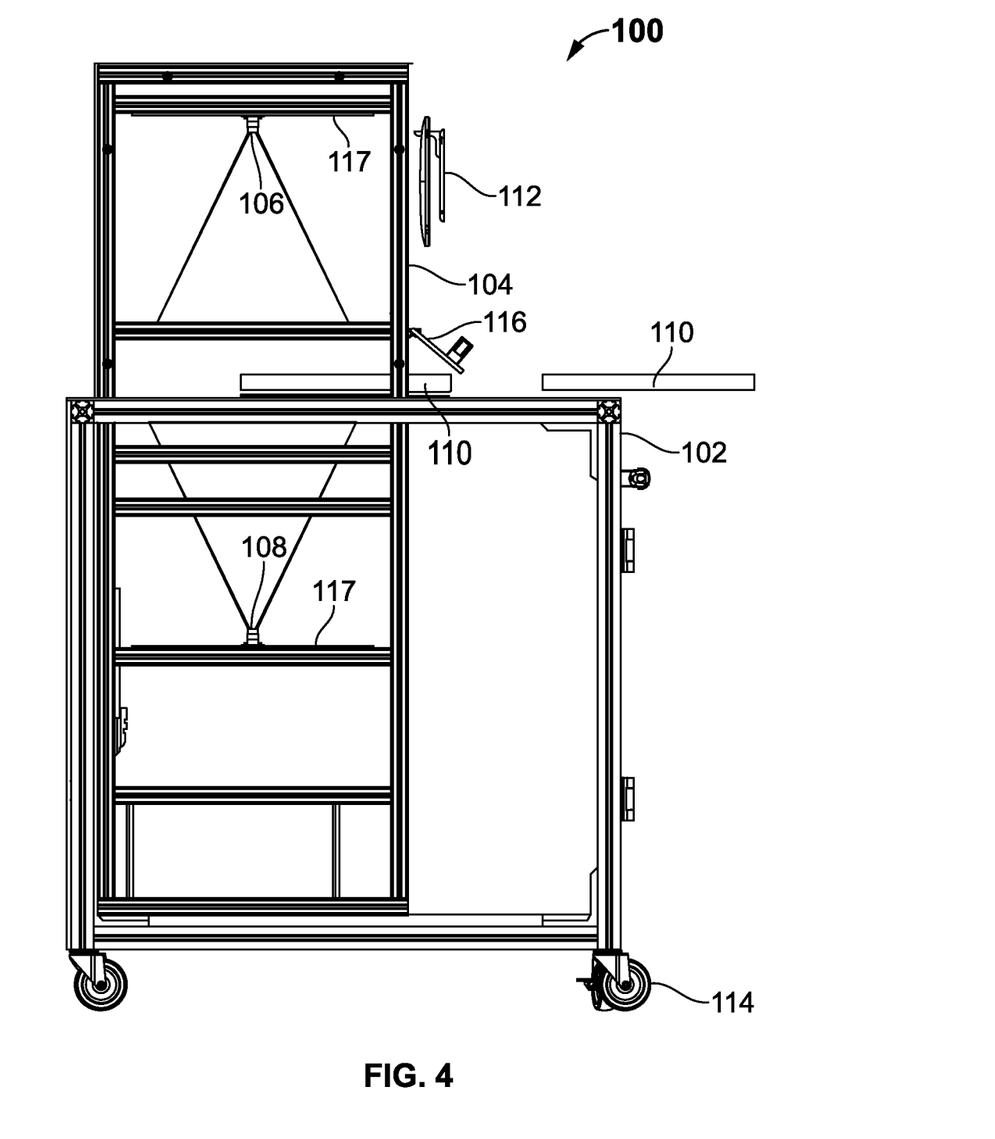

An access door 116 is hingedly supported with the IoT based apparatus frame 102 to provide access to the enclosure 104 to place the tray 110. The touch screen display device 112 is configured to display the veggies or food produce kept for quality assessment. In another embodiment, the top surface of the enclosure 104 or workbench is made of food safe stainless steel to avoid any food contamination. FIG. 3 exemplarily illustrates a see-through front view of the IoT apparatus 100 for assessing the quality of the food produce, in another embodiment of the present invention FIG. 4 exemplarily illustrates a side cross sectional view of the IoT based apparatus 100 for assessing the quality of the food produce, in an embodiment of the present invention. In an embodiment, one or more camera comprises a first camera 106 and a second camera 108. The first camera 106 is mounted at a top portion of the enclosure 104. The second camera 108 is mounted at a bottom portion of the enclosure 104. The apparatus 100 comprises movable camera mounts 117 for mounting the cameras 106, 104. The camera mounts 117 is configured to move between up and down direction or position, so that the distance from the camera lens and the food produce on the tray could be focused properly. This allows to accurately focus on the object or food produce placed in the tray 110. This arrangement enables to capture both top and bottom view of the food produce.

The methodology helps to cover more than 90% of the fruit surface and will effectively reduce the imaging solution to a low-cost alternative instead of having a complete 360-degree coverage with a more expensive orb camera setup, using more than two cameras or using stereoscopic cameras followed by 3D image reconstruction. If the images are taken only from the top, then the defects in the bottom surface of the fruits and vegetables cannot be detected. Hence, the present inventions methodology of capturing the image of both the top and bottom view of the food produce solves this problem.

In another embodiment, one or more cameras are high resolution, 13 Mega Pixel, 4K, USB3 devices, which provides a data transmission rate of around 5 gbps (5 giga bits per second)/640 MBps (Mega Bytes per second). In yet another embodiment, one or more camera is a 6.3 MP camera with 1/1.8" size sensor to reduce distortion around the peripheral region of the tray. In most of the conventional devices, USB2 cameras were used. The present invention utilizes high resolution USB3 cameras to provide machine vision and seamless video transmission capability at 60 FPS (frames per second) to the touchscreen display 112 for a seamless user experience. The high-resolution images provide the deep learning software model an ability to train and detect micro-parametrical defects of the food produce. In yet another embodiment, one or more camera is a plug-and-play camera. Further, the one or more camera has a dedicated, high-performance Image Signal Processor chip (ISP), that performs all the auto functions such as auto white balance, auto exposure control. The ISP and sensor settings have been fine tuned to generate best-in-class video.

In an embodiment, the one or more light source comprises a first light source and a second light source. In another embodiment, the present invention uses two variants of food safe clear plastic tray, which has a light transmission of either greater than 86% or greater 92%, so the image taken from the bottom second camera 108 are clear, without loss in the image quality. This ensures a clear view of the defects in the fruits, which may occur in the bottom view. In another embodiment, the tray 110 is a food safe, which could slide in and out of the enclosure 104. In yet another embodiment, the tray 110 is made using PETG grade plastic or acrylic which is a non-PVC (non-polyvinyl chloride) and non-BPA (non-Bisphenol A).

Figure 5:
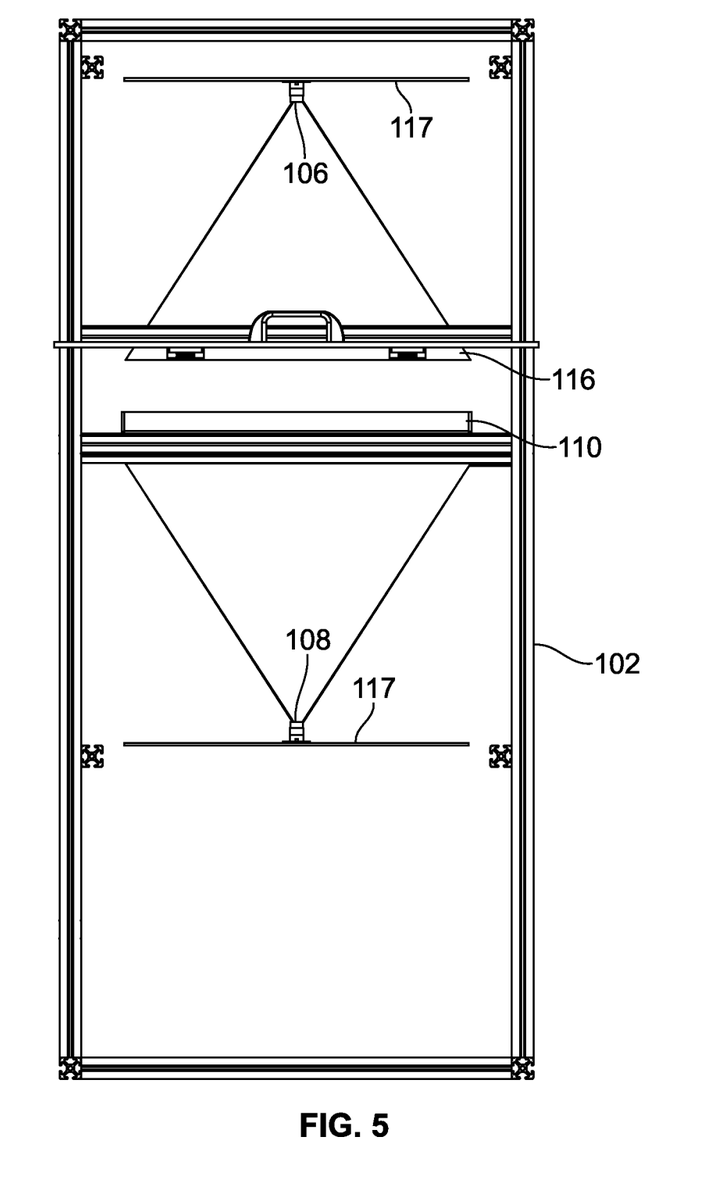
FIG. 5 exemplarily illustrates a see-through front view of the enclosure, in an embodiment of the present invention.
Figure 6:
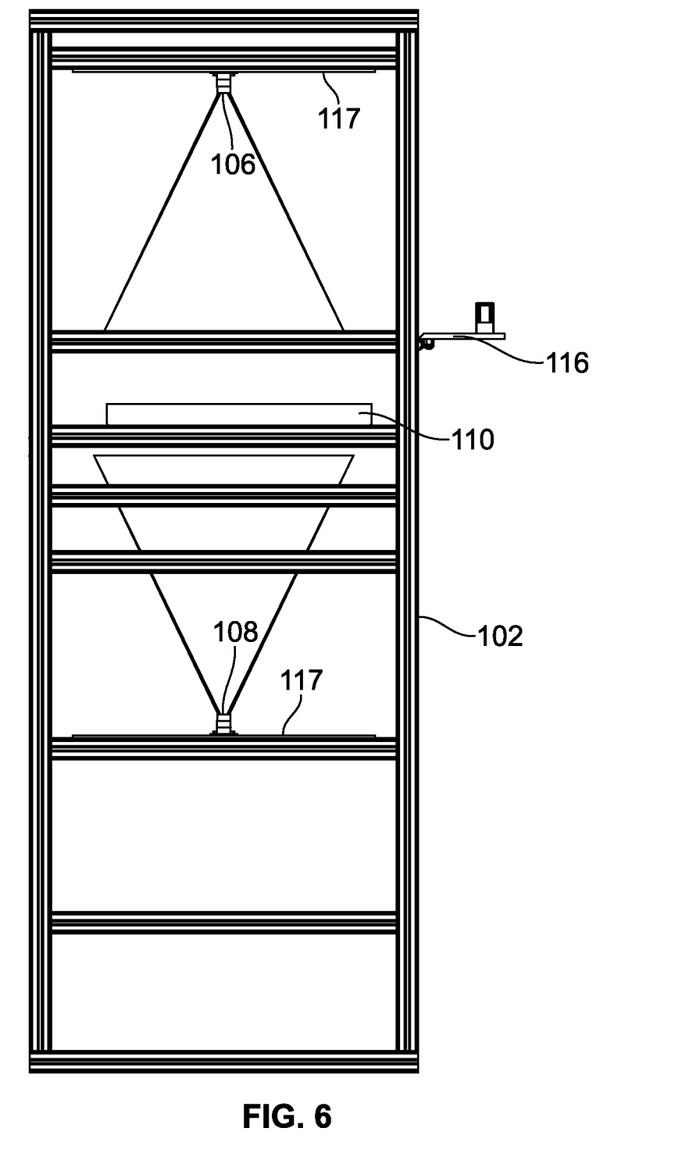
FIG. 6 exemplarily illustrates a see-through side view of the enclosure, in an embodiment of the present invention.

Further, the overall background of the enclosure 104 is configurable. In another embodiment, the background of the enclosure 104 could be of any colored plastic liner, such as, white, black, gray and other colored backgrounds. In some embodiments, the plastic tray 110 is a clear plastic tray or a transparent plastic tray. Since the plastic tray 110 is clear and allows high percentage of light transmission, the fruits and vegetables (our objects) against the chosen background stand out and so are the defects. Preferably, white background is used, but have the flexibility of replacing the background with other colors if that would be more beneficial for object detection and defect identification In another embodiment, the first and second light source are strategically mounted within the enclosure 104 to avoid reflection and hot spots. In another embodiment, the first light source is disposed at the top portion of the enclosure 104. In another embodiment, the second light source is disposed at the bottom portion of the enclosure 104. A see-through front and side view of the enclosure 104 is illustrated in FIG. 5 and FIG. 6, respectively. In an embodiment, the first and second light source is a LED strip. In another embodiment, the first and second light source are placed at an optimal proximity from the tray 110 to properly illuminate fresh produce and also minimize reflections of the light source from the clear plastic tray 110. The LED strips are mounted at an angle of 45 degree to the plane of the tray 110 for brighter illumination.

The position of the LED strips is strategically chosen around 4" (configurable) from the tray level along the 4 sides of the enclosure 104 and both above and below the tray level, so that the reflection of the ceiling on the clear plastic is prevented. If the LED strips are mounted on the ceiling and the floor of the enclosure 104, then once the LED is illuminated, the reflection of the ceiling or the floor along with the side struts of the enclosure 104 is captured in the image, which spoils the overall quality of the image.

In another embodiment, the LED strips are positioned to emit light away from the food produce. This arrangement provides backlighting to the food produce or the image scene and creates an ambient lighting condition. This arrangement further avoids unnecessary shining, gloss on certain section of the food produce such as fruits and vegetables, unnecessary artifacts that hides the actual defects or create unnecessary ones, which in turn may spoils the prediction of the defects by the AI algorithm. In another embodiment, the LED strips are covered by a diffuser of a special grade, which further scatters the light to create a more diffused ambient light and reduce the hot spots and glare from the imaging scene.

The LED strips are also mounted away from the clear tray 110 horizontally by around 2" (configurable) so that the LED themselves do not shine on the tray 110 and create hot spots. The LEDs light source is close to sunlight at 5500K-6000K (daylight white) and have a color rendering index (CRI) of 90+, which will help us take pictures under a consistent close to daylight lighting condition, while preserving the true color of the objects or food produce such as fruits and vegetables. In one embodiment, a color characteristic of the LED strips is chosen depending on the use case, and to accentuate the bright colors of fruits and vegetables. In another embodiment, the LED strips comprises warm white color characteristics with a temperature range of 3000K-3500K. The enclosure 104 with the LEDs and the top and bottom cameras 106, 108 will allow us to take images under a consistent ambient lighting condition, while preserving the true color of the objects, so that defect identification algorithms could work much better on the images of the food produce.

In an embodiment, IoT apparatus 100 could be connected to a wireless network such as internet with the help of the SBC 118 and process images in the cloud using our deep learning pre-trained model. As the SBC 118 is connected to the internet, other devices like tablets, smartphones and other embedded devices could also easily connect with the apparatus 100. This will help in distributing the defect analysis scores and the defects labeled on the images to every interested party in the food supply chain for a particular produce.

Figure 7:
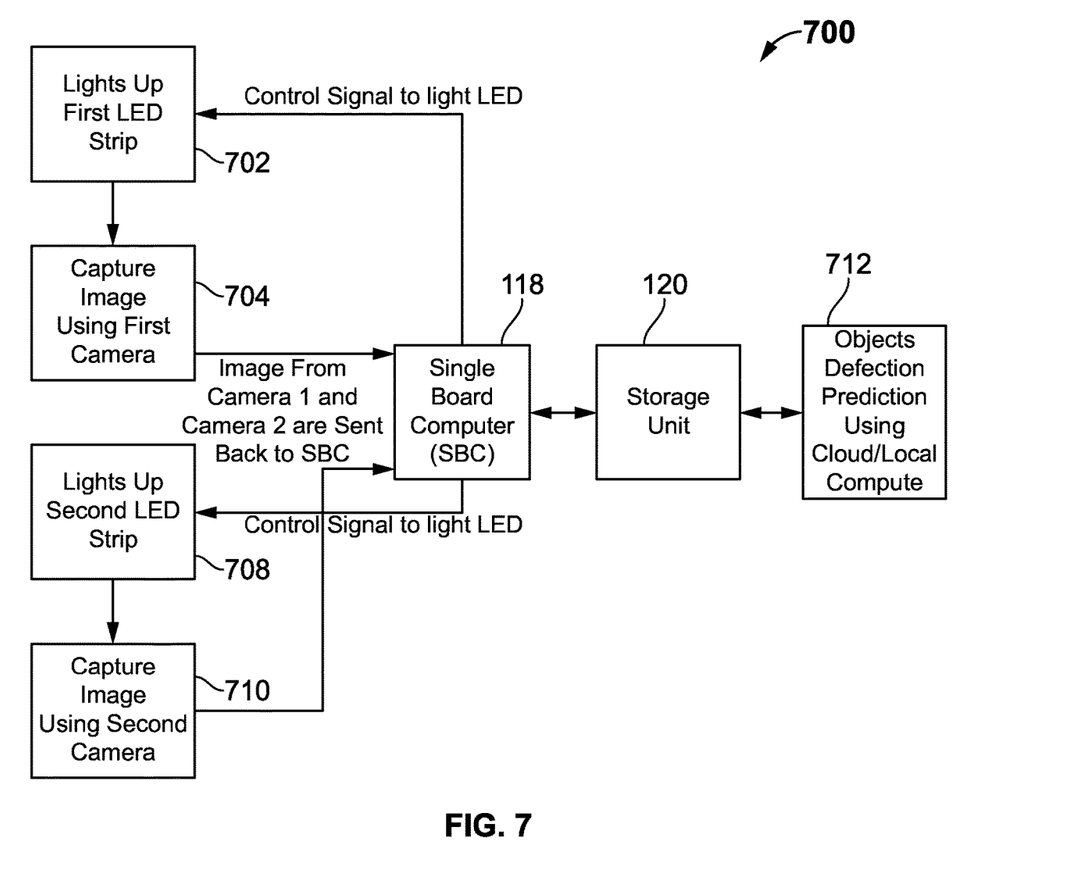
FIG. 7 is a block diagram of a system for inspecting quality of food produce, in an embodiment of the present invention.

FIG. 7 is a block diagram 700 for inspecting quality of food produce, in an embodiment of the present invention. In an embodiment, the apparatus comprises enclosure 104 installed with cameras 106, 108 and one or more light source such as LEDs. First camera 106 is suspended from the upper portion and the second camera 108 from the lower portion.

The cameras 106, 108 are supported from both directions with LEDs and the movable tray 110 is disposed at a middle portion of the enclosure 104. The apparatus 100 further comprises least one storage unit 120, the touch screen display 112 and a single board computer 118 coupled to the camera 106, 108, the first light source, the second light source, the touch screen display 112.

The single board computer (SBC) 118 acts as a controller and processing unit of the apparatus 100. In an embodiment, the SBC 118 comprises an Intel quad-core 64-bit x86 processor in 14 nm process technology with a power dissipation of 5-6 watts. It provides 32 GB eMCC storage along with 4 GB of DDR3L dual-channel RAM. The SBC 118 is also Arduino compatible, powered by Intel Curie microcontroller and GPIO pins which are used to drive the LED controls. The SBC 118 is configured to stream the video of the food produce placed on the tray 110 to the touch screen display 112. The SBC 118 drives the GPIO pin to light up the top LED strip 702. An image of the food produce is captured using the first camera 106 mounted on the ceiling of the enclosure 104 and stores it in the eMCC storage/storage unit 120.

The first camera 106 captures the top side of the food produce 704 placed in the tray 110. Then, the SBC 118 drives the GPIO pin to light up the bottom LED strip 708. An image of the food produce is captured using the second camera 108 mounted at the bottom of the enclosure 104 and stores it in the storage unit 120. The second camera captures the bottom side of food produce 710. The captured images from the camera 106, 108 will be transferred to the single board computer 118. A deep learning pre-trained model is run on those images to perform defect prediction 712 and provide defect score for each defect. The per defect score and the total score is then sent back to SBC 118, which is then displayed on the touch screen display 112 along with the images with the defects labeled on the images.

Figure 8:
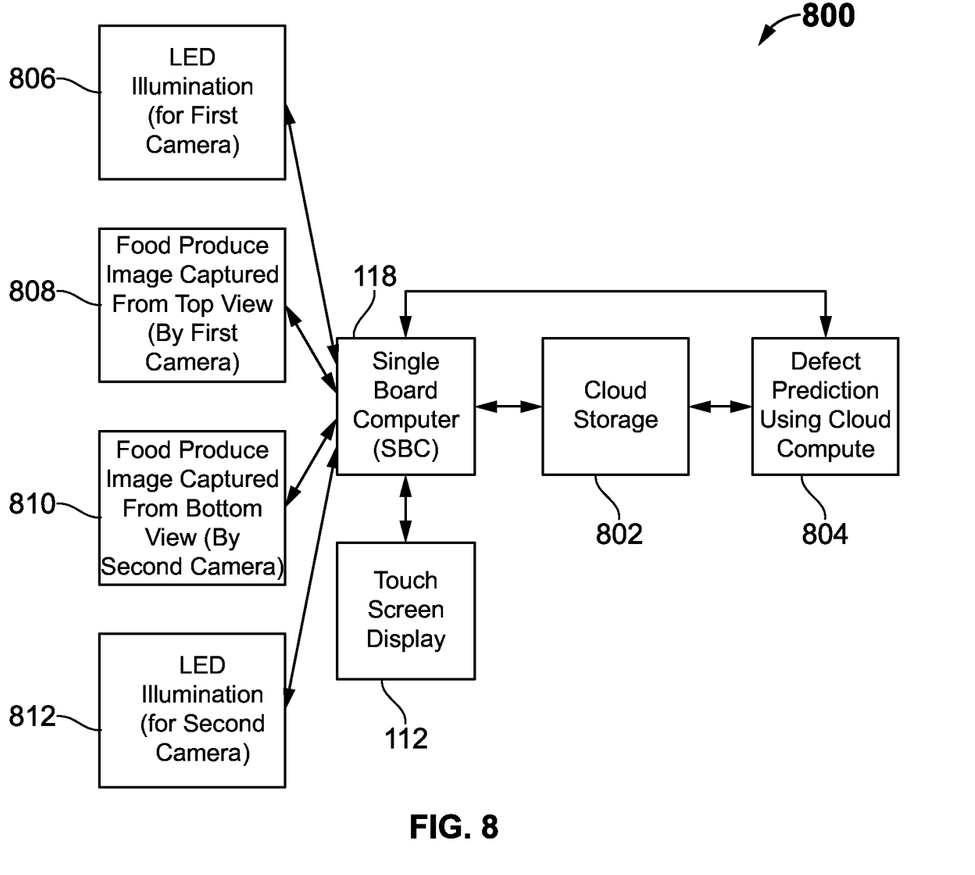
FIG. 8 is a block diagram of a system for inspecting quality of food produce using cloud compute, in an embodiment of the present invention.
Figure 9:
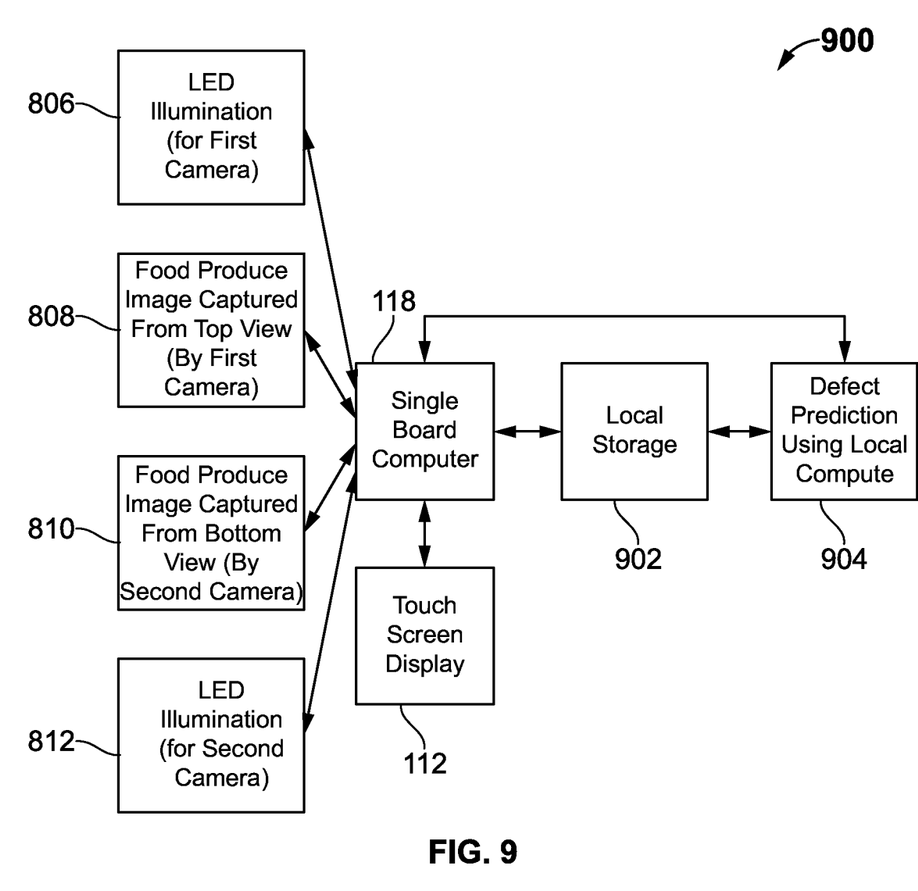
FIG. 9 is a block diagram of a system for inspecting quality of food produce using local compute, in an embodiment of the present invention.

FIG. 8 is a block diagram 800 for inspecting the quality of food produce using cloud compute, in an embodiment of the present invention. The LED strips are illuminated on receiving a signal from the single board computer 118, as shown in 806, 812. Then the image of the produce is captured from the camera 106, 108 and would be transferred to the single board computer 118, as shown in block 808, 810. The image is saved into a cloud storage 802. A cloud compute algorithm executes the images for defect prediction 804. FIG. 9 is a block diagram 900 for inspecting the quality of food produce using local compute, in an embodiment of the present invention. The image from the camera 106, 108 is saved into a local storage 902. A local compute algorithm executes the images for defect prediction 904. The computed prediction is again transferred to the single board computer 118 for displaying the prediction in the touch screen display 112. In another embodiment, the image stored from the camera 106, 108 in the local storage 902, could be transferred to the cloud storage such as Amazon AWS, Google Cloud etc., using programs in the SBC 118.

Preferred embodiments of this invention are described herein, including the best mode known to the inventors for carrying out the invention. It should be understood that the illustrated embodiments are exemplary only, and should not be taken as limiting the scope of the invention.

The foregoing description comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

What is claimed is:

1. An IoT based apparatus for inspecting quality of food produce, comprising:
   a frame having an enclosure
   a movable plastic tray disposed at a middle portion of the enclosure, configured to receive a food produce to be inspected;
   one or more camera comprising a first camera and a second camera installed within the enclosure;
   one or more light source comprises a first light source and a second light source strategically mounted within the enclosure to avoid reflection and hot spots,
   at least one storage unit for storing the image of food produce from the one or more camera;
   a touch screen display for displaying the food produce placed in the tray;
   a single board computer coupled to the camera, the first light source, the second light source, the touch screen display, a wireless network, configured to,
   light the first light source to emit light and capture image of an upper region of the food produce placed in the tray;
   light the second light source to emit light and capture image of a lower region of the food produce placed in the tray;
   store the at least two captured images in the storage unit and analyze the at least two captured images to obtain defect value of the food produce, using a deep learning model; and
   display the defect value and the food produce image along with defects labelled on the image.

2. The apparatus of claim 1, wherein the first camera installed at an upper portion of the enclosure and the second camera installed at a lower portion of the enclosure.

3. The apparatus of claim 1, wherein the first light source disposed at the top portion of the enclosure and the second light source disposed at the bottom portion of the enclosure.

4. The apparatus of claim 1, wherein each light source is secured within the enclosure via a movable camera mount.

5. The apparatus of claim 4, wherein the movable camera mount is configured to move between an up and down position to focus the food produce placed in the tray.

6. The apparatus of claim 1, further comprises four or more wheels beneath the frame of the enclosure to facilitate movement of the apparatus.

7. The apparatus of claim 1, wherein the single board computer is configured to drive the one or more light source and one or more camera in sequence to capture the two least two images of the food produce.

8. The apparatus of claim 1, wherein the first and second light source is configured to emit warm white color with temperature of 3000K-3500K to preserve the natural color food produce.

9. The apparatus of claim 1, wherein the single board computer is configured to superimpose the captured image of the upper region of the food produce to the captured image of the lower region of the food produce to obtain a 360-degree coverage of the food produce.

10. The apparatus of claim 1, wherein the plastic tray is a transparent plastic tray and allows high percentage of light transmission.

11. The apparatus of claim 1, wherein the first light source and the second light source is a LED strip.

12. The apparatus of claim 1, wherein the first light source and the second light source are mounted at an angle of 45 degree to a plane of the plastic tray for brighter illumination.

13. The apparatus of claim 1, wherein the first light source and the second light source are covered by a diffuser.

14. An IoT based apparatus for inspecting quality of food produce, comprising:
 a frame having an enclosure
 a movable plastic tray disposed at a middle portion of the enclosure, configured to receive a food produce to be inspected;
 one or more camera comprising a first camera and a second camera installed within the enclosure,
  wherein the first camera installed at an upper portion of the enclosure and the second camera installed at a lower portion of the enclosure;
 one or more light source comprises a first light source and a second light source strategically mounted within the enclosure to avoid reflection and hot spots,
  wherein the first light source disposed at the top portion of the enclosure and the second light source disposed at the bottom portion of the enclosure;
 at least one storage unit for storing the image of food produce from the one or more camera;
 a touch screen display for displaying the food produce placed in the tray;
 a single board computer coupled to the camera, the first light source, the second light source, the touch screen display, a wireless network, configured to,
  light the first light source to emit light and capture image of an upper region of the food produce placed in the tray;
  light the second light source to emit light and capture image of a lower region of the food produce placed in the tray;
  store the captured image in the storage unit and analyze the at least two captured images to obtain defect value of the food produce, using a deep learning model; and
  display the defect value and the food produce image along with defects labelled on the image.

15. The apparatus according to claim 14, further comprises four or more wheels beneath the frame of the enclosure to facilitate movement of the apparatus.

16. The apparatus of claim 14, wherein each light source is secured within the enclosure via a movable camera mount.

17. The apparatus of claim 16, wherein the movable camera mount is configured to move between an up and down position to focus the food produce placed in the tray.

18. The apparatus of claim 14, wherein the first light source and the second light source are mounted at an angle of 45 degree to a plane of the plastic tray for brighter illumination.

19. The apparatus of claim 14, wherein the single board computer is configured to superimpose the captured image of the upper region of the food produce to the captured image of the lower region of the food produce to obtain a 360-degree coverage of the food produce.

20. The apparatus of claim 14, wherein the first and second light source is configured to emit warm white color with temperature of 3000K-3500K to preserve the natural color food produce.

* * * * *